United States Patent [19]

Nardi et al.

[11] Patent Number: 5,663,372
[45] Date of Patent: Sep. 2, 1997

[54] PROCESS FOR THE PREPARATION OF 5-AMINO-1,3-DIOXANES

[75] Inventors: Antonio Nardi, Paderno Dugnano; Marco Villa, Milan, both of Italy

[73] Assignee: Zambon Group S.p.A., Vicenza, Italy

[21] Appl. No.: 722,174

[22] PCT Filed: Apr. 5, 1995

[86] PCT No.: PCT/EP95/01246
§ 371 Date: Oct. 10, 1996
§ 102(e) Date: Oct. 10, 1996

[87] PCT Pub. No.: WO95/28395
PCT Pub. Date: Oct. 26, 1995

[30] Foreign Application Priority Data

Apr. 14, 1994 [IT] Italy .................... MI94A0699

[51] Int. Cl.$^6$ .................... C07D 319/06; C07D 319/08; C07C 213/02; C07C 213/08

[52] U.S. Cl. .................... 549/333; 549/371; 564/487
[58] Field of Search .................... 549/371, 333

[56] References Cited

U.S. PATENT DOCUMENTS 2,370,586  4/1945  Senkus .................... 549/333
5,580,993  12/1996  Villa et al. .................... 549/371

*Primary Examiner*—Johann Richter
*Assistant Examiner*—Laura L. Stockton
*Attorney, Agent, or Firm*—Oblon, Spivak, McClelland, Maier & Neustadt, P.C.

[57] ABSTRACT

Described herein is a process for the preparation of 5-amino-1,3-dioxanes of formula (I), wherein R and $R_1$ have the meanings reported in the description, comprising the catalytic hydrogenation of the new oximes of formula (II).

8 Claims, No Drawings

PROCESS FOR THE PREPARATION OF 5-AMINO-1,3-DIOXANES

This application is a 371 of PCT/EP95/01246 filed Apr. 5, 1995.

BACKGROUND OF THE INVENTION

1. Field of the Invention

The present invention relates to a process for the preparation of acetals of 2-amino-1,3-propanediol and, more particularly, it relates to a process for the preparation of 5-amino-1,3-dioxanes. The acetals of 2-amino-1,3-propanediol are advantageously used as synthetic intermediates in the preparation of the compound (S)-N,N'-bis-[2-hydroxy-1-(hydroxymethyl) ethyl]-5-[(2-hydroxy-1-oxopropyl)-amino]-2, 4,6-triiodo-1,3-benzenedicarboxamide, known with its International Nonproprietary Name Iopamidol (The Merck Index, XI Ed., page 799, No. 4943).

2. Discussion of the Background

Iopamidol was described for the first time by the Swiss Company Savac A. G. in the British patent No. 1,472,050 and is used in diagnostics as a non-ionic X-ray contrast medium.

The preparation of Iopamidol, described in said patent, comprises the condensation reaction of L-5-(2-acetoxypropionylamino)-2, 4,6-triiodo-isophthalic acid dichloride with 2-amino-1,3-propanediol, better known as serinol, in dimethylacetamide and in the presence of a base.

Alternatively, in the same patent, a method comprising the condensation reaction of the above acid dichloride with an acetal of serinol is described; the subsequent acid hydrolysis of the resultant diacetal, carried out according to conventional techniques, allows then to obtain the desired product.

Among the possible acetals of serinol which can be used in said synthesis, for instance, 5-amino-1,3-dioxanes are cited.

Several processes for the preparation of 5-amino-1,3-dioxanes are reported in the literature.

The British patent application No. 2,081,256 (Rhône-Poulenc Industries) and the U.S. Pat. No. 3,812,186 (Eprova A. G.) describe the preparation of 5-amino-2,2-dialkyl-1,3-dioxanes by catalytic hydrogenation of the corresponding 5-nitro derivatives which, in turn, are prepared by direct cyclization of 2-nitro-1,3-propanediol with a suitable ketone, in the presence of boron trifluoride etherate.

In the U.S. Pat. No. 4,978,793 (W. R. Grace & Go.) it is described a preparation of 5-amino-2,2-dialkyl-1,3-dioxanes which comprises at first the synthesis of the corresponding 5-nitro derivatives, through a three step process starting from nitromethane and formaldehyde, and, subsequently, the reduction of the nitro group.

The processes for the preparation of 5-amino-1,3-dioxanes described in the literature evidence the remarkable drawback of using nitro derivatives, which are particularly unstable and explosive compounds, as intermediates.

Processes for the preparation of primary amines comprising the reduction of the corresponding oximes are also known in the literature.

Said reductions can be carried out by using conventional reducing agents or by means of catalytic hydrogenation [M. Hudlicky, Reduction in Organic Chemistry, Academic Press, (1984)].

Nevertheless, to the extent of our knowledge, the preparation of acetals of serinol through the reduction of the corresponding oximes has been never described in the literature.

SUMMARY OF THE INVENTION

Now we have found and it is the object of the present invention a process for the preparation of 5-amino-1,3-dioxanes of formula

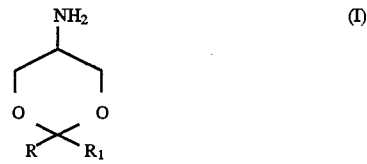

wherein

R and $R_1$, the same or different, represent a hydrogen atom, a straight or branched $C_1$–$C_4$ alkyl, an optionally substituted phenyl or, together with the carbon atom to which they are bonded, form a $C_5$–$C_6$ cycloaliphatic ring, comprising the reduction of the oximes of formula

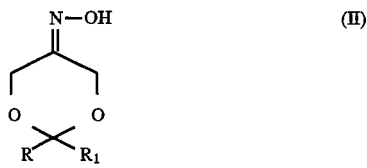

wherein R and $R_1$ have the above reported meanings, by catalytic hydrogenation in a suitable solvent.

The compounds of formula I can be optionally hydrolyzed to serinol according to conventional techniques.

DETAILED DESCRIPTION OF THE PREFERRED EMBODIMENTS

Either the serinol or the amino acetals of formula I are useful intermediates in the preparation of Iopamidol as described, for instance, in the aforementioned British patent No. 1,472,050. With the term acetal, we intend a compound obtained by reacting an alcohol, or even a diol, with either a ketone or an aldehyde (IUPAC Nomenclature of Organic Chemistry, 1979 Edition, Rule C-331, page 178).

With the term catalytic hydrogenation we intend a reduction reaction carried out in the presence of catalysts, wherein the reducing agent is hydrogen (J. March, Advanced Organic Chemistry, IV Ed., 1026). The process object of the present invention is of easy industrial application and the compounds of formula I and II, being stable, do not present the risk of explosions during the accomplishment of the process.

Specific examples of the compounds of formula I obtainable according to the process object of the present invention are:

5-amino-2,2-dimethyl-1,3-dioxane
5-amino-2,2-diethyl-1,3-dioxane
5-amino-2-ethyl-2-methyl-1,3-dioxane
5-amino-2-phenyl-1,3-dioxane
3-amino-1,5-dioxaspiro[5.5]undecane
3-amino-1,5-dioxaspiro[4.5]decane The 1,3-dioxan-5-one oximes of formula II are new and they are a further object of the present invention.

Said compounds can be prepared by direct acetalization of 1,3-dihydroxyacetone oxime with a ketone or with an aldehyde in the presence of an acid.

It is clear to the man skilled in the art that the meanings of both R and $R_1$ substituents, for the compounds of formula I and II, will depend on the selected aldehyde or ketone.

In this connection, it is worth noting that, since the use to which the compounds of formula I are intended comprises their hydrolysis with loss of the R—CO—$R_1$ fragment, the nature of the groups R and $R_1$ is of little importance and their selection will be substantially guided by economic and availability criteria.

Specific examples of aldehydes or ketones which can be used in the above acetalization reaction are, for instance, formaldehyde, acetaldehyde, benzaldehyde, 4-methoxybenzaldehyde, 2-methylbenzaldehyde, acetone, butanone, 2-pentanone, 3-pentanone, cyclopentanone, cyclohexanone, acetophenone and benzophenone.

Alternatively, the preparation of 1,3-dioxan-5-one oximes of formula II can be carried out, in a preferred way, by reacting the corresponding 1,3-dioxan-5-ones with hydroxylamine hydrochloride, according to the methods usually adopted in the preparation of the oximes (J. March, Advanced Organic Chemistry, IV Ed., 906–907).

The above 1,3-dioxan-5-ones are known compounds and are prepared according to known methods [D. Hoppe et al., Tetrahedron, 45 (3), 687–694, (1989)].

The oximes of formula II according to the process object of the present invention are then catalytically hydrogenated to the compounds of formula I, in the presence of suitable reaction solvents.

Examples of employable catalysts are those commonly used in the reactions of catalytic hydrogenation.

Preferably, rhodium on alumina, Raney nickel and palladium on charcoal are used.

The catalyst is used in amounts preferably comprised between 0.001 and 0.01 moles per mole of substrate to be hydrogenated, i.e. the selected 1,3-dioxan-5-one oxime of formula II.

Larger amounts of catalyst, for instance up to 10–15% in moles with respect to the substrate, can also be used.

The hydrogenation reaction according to the process object of the present invention is carried out, as previously pointed out, in the presence of suitable inert solvents.

With the term inert solvents we intend the solvents which do not undergo chemical reactions with the reagents or with the reaction products.

Suitable solvents are those commonly used in the reactions of catalytic hydrogenation such as, for instance, lower $C_1$–$C_4$ alcohols. Methanol and ethanol are preferably used.

Pressure and temperature do not represent critical parameters of the reaction.

Preferably, the hydrogenation is carried out at a pressure comprised between 1 and 10 bars ($10^5$–$10^6$ Pa) and at a temperature comprised between 20° C. and 80° C.

More drastic conditions of pressure and temperature are equally effective but useless.

In a practical embodiment, the process object of the present invention is carried out according to the following operating conditions. A suitable amount of the compound of formula II in a suitable solvent (for instance methanol) is loaded into a reactor suitable to sustain internal pressures, and a suitable amount of catalyst is then added.

The resultant system is put under hydrogen atmosphere according to the commonly used techniques and kept under stirring for a few hours (5–24) at the preselected temperature and pressure [for instance 60° C. and 7 bars (7·$10^5$ Pa)].

Due to the following practical features such as, for instance, the easy industrial application, the accessibility of the starting material, the stability of the reagents and of the reaction products and the simple work-up of the reaction mixture, the present invention makes available a very advantageous process for the preparation of 5-amino-1,3-dioxanes.

With the aim to better illustrate the present invention, without however limiting it, the following examples are now given.

EXAMPLE 1

Preparation of 2,2-dimethyl-1,3-dioxan-5-one oxime

Hydroxylamine hydrochloride (5 g; 71.9 mmoles) was added, under stirring and in 30 minutes, to a solution of 2,2-dimethyl-1,3-dioxan-5-one (6.2 g; 47.7 mmoles) in pyridine (6.75 g; 85.4 moles), keeping the temperature at 15° C.

At the end, the reaction mixture was kept under stirring at 25° C. for 4 hours.

Methylene chloride (30 ml) and water (15 ml) were subsequently added, maintaining the stirring for further 5 minutes.

The phases were separated and the organic phase, washed with water (10 ml), was dried on anhydrous sodium sulphate and evaporated at reduced pressure.

2,2-Dimethyl-1,3-dioxan-5-one oxime (6.7 g) was thus obtained (97.5% $^1$H-NMR titre, 95% yield).

$^1$H-NMR (300 MHz, DMSO-$d_6$): δ (ppm): 1.33 (s, 6H); 4.19 (s, 2H); 4.46 (s, 2H); 10.82 (s, 1H).

IR (NEAT): significative bands at 3360, 1440, 1380 cm$^{-1}$

By working in a similar way but using 1,3-dioxan-5-one, 2,2-diethyl-1,3-dioxan-5-one and 1,5-dioxaspiro[5,5] undecan-3-one, in place of 2,2-dimethyl-1,3-dioxan-5-one, the following compounds were respectively obtained: 1,3-dioxan-5-one oxime, 2,2-diethyl-1,3-dioxan-5-one oxime and 1,5-dioxaspiro[5,5]undecan-3-one oxime.

EXAMPLE 2

Preparation of 5-amino-2,2-dimethyl-1,3-dioxane 2,2-Dimethyl-1,3-dioxan-5-one oxime (5 g; 34.4 mmoles), prepared as described in example 1, methanol (40 ml) and rhodium supported on alumina at 5% (0.35 g; 0.17 mmoles) were respectively loaded into a reactor provided with mechanical stirring.

After removing the surrounding air, hydrogen at a pressure of 7 bars (7·$10^5$ Pa) was added.

The resultant system was thus kept under stirring at 60° C. for 5 hours.

At the end of the reaction, after emptying the reactor, the catalyst was filtered off on a celite bed and the solvent was evaporated at reduced pressure.

A crude product (5 g) constituted by 5-amino-2,2-dimethyl-1,3-dioxane (65% G. C. titre, 72% yield), according to gas-chromatographic analysis, was thus obtained.

The desired product was then isolated by distillation of the reaction crude at 75° C. and 12 mm/Hg.

We claim:

1. A process for the preparation of a 5-amino-1,3-dioxane of formula

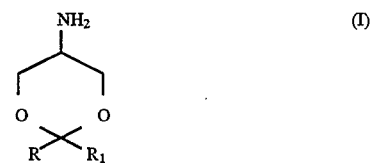

wherein

R and $R_1$, the same or different, represent a hydrogen atom, a straight or branched $C_1$–$C_4$ alkyl, an optionally substituted phenyl or, together with the carbon atom to which they are bonded, form a $C_5$–$C_6$ cycloaliphatic ring, comprising the reduction of an oxime of formula wherein R and R₁ have the above reported meanings, by catalytic hydrogenation in a suitable solvent.

2. A process according to claim 1 wherein the catalytic hydrogenation is carried out by using rhodium on alumina, Raney nickel or palladium on charcoal.

3. A process according to claim 1 wherein the catalyst consists of rhodium supported on alumina at 5%.

4. A process according to claim 1 wherein the catalyst is used in amounts comprised between 0.001 and 0.01 moles per mole of substrate to be hydrogenated.

5. A process according to claim 1 wherein the reaction solvent is a lower $C_1$–$C_4$ alcohol.

6. A process according to claim 1 wherein the solvent is methanol or ethanol.

7. A process according to claim 1 wherein the hydrogenation reaction is carried out at a pressure comprised between 1 and 10 bars ($10^5$–$10^6$ Pa) and at a temperature between 20° C. and 80° C.

8. A process for the preparation of a 5-amino-1,3-dioxane of formula

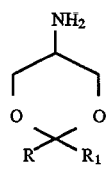

(I)

wherein

R and R₁, the same or different, represent a hydrogen atom, a straight or branched $C_1$–$C_4$ alkyl, an optionally substituted phenyl or, together with the carbon atom to which they are bonded, form a $C_5$–$C_6$ cycloaliphatic ring, comprising the reduction of an oxime of formula

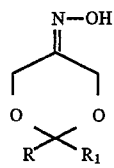

(II)

wherein R and R₁ have the above reported meanings, by catalytic hydrogenation in the presence of rhodium supported on alumina, at a pressure comprised between 1 and 10 bars ($10^5$–$10^6$ Pa) and at a temperature between 20° C. and 80° C., in a lower $C_1$–$C_4$ alcohol.

* * * * *